United States Patent
Harrod, IV

(10) Patent No.: US 11,890,114 B2
(45) Date of Patent: Feb. 6, 2024

(54) SYSTEM AND METHOD FOR CLASSIFYING AND MANAGING MEDICAL APPLICATION DISCONNECTS

(71) Applicant: KONINKLIJKE PHILIPS N.V., Eindhoven (NL)

(72) Inventor: John Price Harrod, IV, North Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 605 days.

(21) Appl. No.: 17/084,696

(22) Filed: Oct. 30, 2020

(65) Prior Publication Data
US 2021/0128071 A1    May 6, 2021

Related U.S. Application Data

(60) Provisional application No. 62/929,131, filed on Nov. 1, 2019.

(51) Int. Cl.
*A61B 5/00* (2006.01)
*G16H 40/20* (2018.01)

(52) U.S. Cl.
CPC .......... *A61B 5/7264* (2013.01); *A61B 5/0022* (2013.01); *A61B 5/7275* (2013.01); *G16H 40/20* (2018.01)

(58) Field of Classification Search
CPC ... G06F 11/0736; G06F 11/079; G16H 40/20; G16H 40/67; A61B 5/0022; A61B 5/7275; G06N 20/00; G06N 5/04
See application file for complete search history.

(56) References Cited

U.S. PATENT DOCUMENTS

| | | | |
|---|---|---|---|
| 6,662,089 B2 | 12/2003 | Felke et al. | |
| 6,665,820 B1 | 12/2003 | Frowein et al. | |
| 9,037,922 B1* | 5/2015 | Cabrera | G06F 11/076 714/47.1 |
| 2007/0027653 A1 | 2/2007 | Godara | |
| 2007/0043535 A1* | 2/2007 | Belden | G06F 11/349 702/183 |
| 2010/0249551 A1 | 9/2010 | Miller | |
| 2012/0212596 A1* | 8/2012 | Mathur | A61B 5/7465 348/E7.085 |
| 2017/0269983 A1* | 9/2017 | Liu | H04L 41/00 |
| 2018/0150548 A1* | 5/2018 | Shah | G06F 16/285 |
| 2019/0196893 A1* | 6/2019 | Lee | G06F 11/0751 |
| 2020/0057689 A1* | 2/2020 | Farahat | G06F 11/0751 |
| 2020/0379871 A1* | 12/2020 | Prakash | G06F 11/366 |
| 2021/0109800 A1* | 4/2021 | Chen | G06F 11/3409 |

* cited by examiner

*Primary Examiner* — Etienne P Leroux

(57) ABSTRACT

A method for processing information includes receiving a feature set for an application in a medical system, determining a disconnection between the application and a monitoring station, and determining a type of the disconnection based on information in the received feature set. The type of disconnection may be determined by inputting the feature set into a classifier trained to automatically determine the type of disconnection based on the information in the feature set. Information indicative of the type of disconnection may then be input into a rules-based engine, which generates a recommendation for remediating or otherwise managing the classified disconnection.

18 Claims, 6 Drawing Sheets ns**

SYSTEM AND METHOD FOR CLASSIFYING AND MANAGING MEDICAL APPLICATION DISCONNECTS

TECHNICAL FIELD

This disclosure relates generally to processing information, and more specifically, but not exclusively, to managing applications used in the care of patients.

BACKGROUND

Healthcare professionals are continually seeking ways to improve the care and management of their patients. One recent trend involves using wireless monitoring devices to keep track of pulse, blood pressure, and other vital signs. This information is transmitted over a network to a central workstation, where nurses can respond when there is a problem.

From time to time, the remote monitoring devices fail or otherwise become non-responsive. When this happens, patients cannot be properly monitored. Presently, there is no way to determine exactly what caused the malfunction. As a result, hospital personnel must physically visit patient rooms and inspect the devices to determine the reasons for the failure. This process is inefficient, especially in cases where the application or other software in the devices have lost connectivity to the network. Current methods do not address these application connectivity issues, which have proven to cause substantial disruptions in the ability to provide adequate patient care.

SUMMARY

A brief summary of various example embodiments is presented below. Some simplifications and omissions may be made in the following summary, which is intended to highlight and introduce some aspects of the various example embodiments, but not to limit the scope of the invention.

In accordance with one embodiment, a method for processing information includes receiving a feature set for an application in a medical system, determining a disconnection between the application and a monitoring station, and determining a type of the disconnection based on information in the received feature set, wherein determining the type of disconnection includes inputting the feature set into a classifier trained to automatically determine the type of disconnection based on the information in the feature set.

The information in the feature set may include a plurality of categories of information relating to the application, wherein each category in the plurality of categories of information is indicative of a different parameter relating to disconnection of the application. The plurality of categories may include one or more of a first category including application state features, a second category including device state features, or a third category including network statistics features. The plurality of categories may include at least two of the first category, the second category, or the third category. The first category may include a plurality of first features, the second category may include a plurality of second features, if in the plurality of categories, the third category may include a plurality of third features, and the type of disconnection of the application may be automatically determined based on a predetermined combination of one or more of the first features of the first category, one or more of the second features of the second category, and one or more features of the third features of the third category, if the third category is in the plurality of categories.

The method may include generating a confidence score indicating a probability for the type of disconnection automatically determined by the classifier. The method may include generating information indicative of a recommended course of action for the type of disconnection determined by the classifier. Generating the information may include inputting information indicative of the type of disconnection into a rules-based engine, wherein the rules-based engine matches the type of disconnection to at least one predetermined rule corresponding to the recommended course of action. The method may include outputting information of the type of disconnection on a display at the monitoring station. The monitoring station may be at one of a technical support location, a nurses station, or a medical monitoring facility.

In accordance with one or more other embodiments, a system for processing information may include a memory configured to store instructions and a processor configured to execute the instructions to: receive a feature set for an application in a medical system; determine a disconnection between the application and a monitoring station; and determine a type of the disconnection based on information in the received feature set, wherein the processor is configured to determine the type of disconnection based on a classifier trained to automatically determine the type of disconnection based on the information in the feature set.

The information in the feature set may include a plurality of categories of information relating to the application, wherein each category in the plurality of categories of information is indicative of a different parameter relating to disconnection of the application. The plurality of categories may include one or more of a first category including application state features, a second category including device state features, or a third category including network statistics features.

The plurality of categories may include at least two of the first category, the second category, or the third category. The first category may include a plurality of first features, the second category may include a plurality of second features, if in the plurality of categories, the third category may include a plurality of third features, and the type of disconnection of the application may be automatically determined based on a predetermined combination of one or more of the first features of the first category, one or more of the second features of the second category, and one or more features of the third features of the third category, if the third category is in the plurality of categories. The processor may be configured to execute the instructions to generate a confidence score indicating a probability for the type of disconnection automatically determined by the classifier. The processor may be configured to execute the instructions to generate information indicative of a recommended course of action for the type of disconnection determined by the classifier.

Generating the information may include inputting information indicative of the type of disconnection into a rules-based engine, wherein the rules-based engine matches the type of disconnection to at least one predetermined rule that corresponds to the recommended course of action. The processor may be configured to execute the instructions to output information indicative of the type of disconnection on a display at the monitoring station. The monitoring station may be at one of a technical support location, a nurses station, or a medical monitoring facility.

BRIEF DESCRIPTION OF THE DRAWINGS

The accompanying figures, where like reference numerals refer to identical or functionally similar elements throughout the separate views, together with the detailed description below, are incorporated in and form part of the specification, and serve to illustrate example embodiments of concepts found in the claims and explain various principles and advantages of those embodiments.

These and other more detailed and specific features are more fully disclosed in the following specification, reference being had to the accompanying drawings, in which.

DETAILED DESCRIPTION

Figure 1:
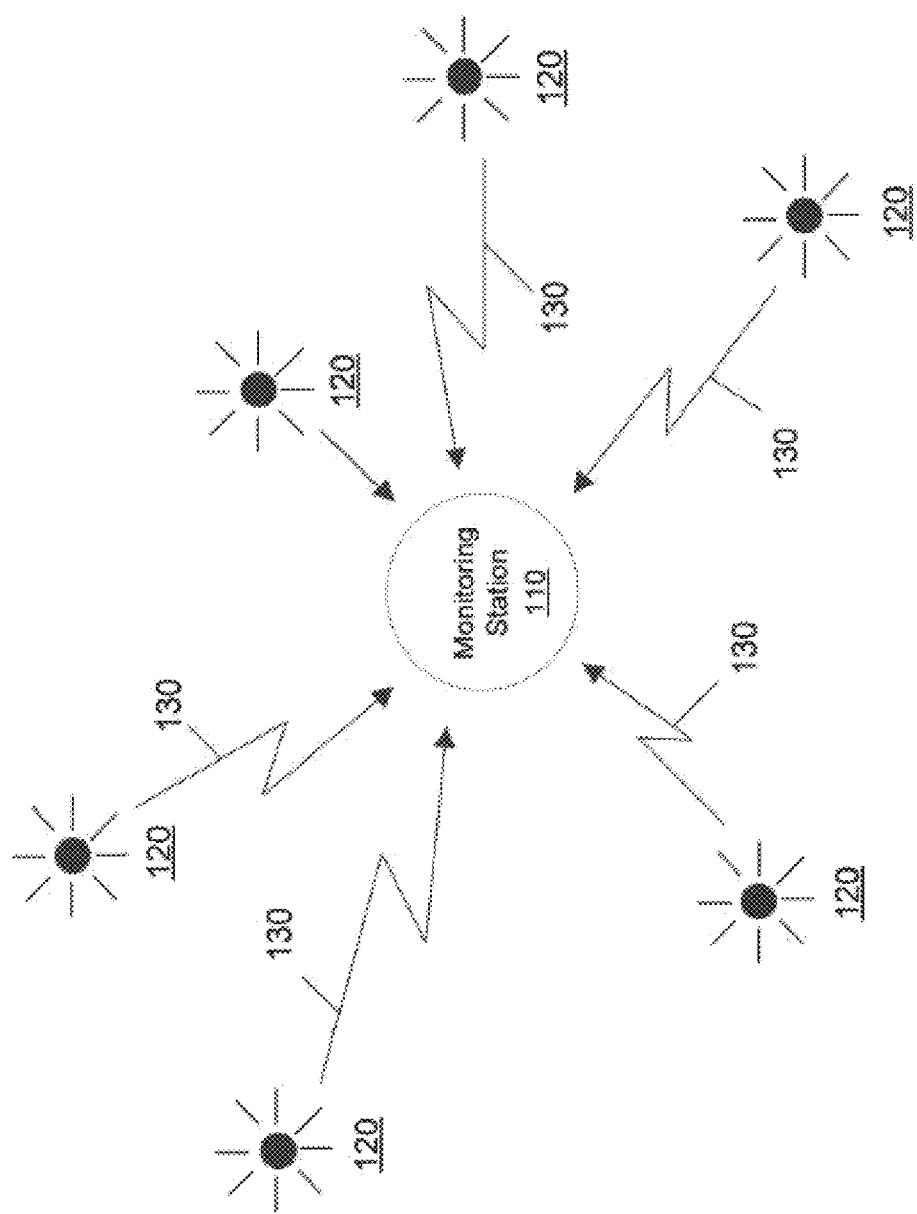
FIG. 1 illustrates an example scenario of embodiments for classifying disconnects.

It should be understood that the figures are merely schematic and are not drawn to scale. It should also be understood that the same reference numerals are used throughout the figures to indicate the same or similar parts.

The descriptions and drawings illustrate the principles of various example embodiments. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various example embodiments described herein are not necessarily mutually exclusive, as some example embodiments can be combined with one or more other example embodiments to form new example embodiments. Descriptors such as "first," "second," "third," etc., are not meant to limit the order of elements discussed, are used to distinguish one element from the next, and are generally interchangeable. Values such as maximum or minimum may be predetermined and set to different values based on the application.

Example embodiments describe a system and method for classifying disconnects between one or more medical systems and at least one monitoring station. The one or more medical systems may include medical equipment and/or applications in a medical system or device that is in communication with the monitoring station over a network or short-range link. In at least one embodiment, the system and method classifies types of disconnections that occur between a clinical medical application irrespective of whether a network connection exists between the host medical system of the application and the monitoring station. For example, in one case the system and method may detect and classify a type of disconnection of the application when the host system is still operative and/or connected to the network. In another case, the system and method may confirm a connection of the application even when the host medical system was disconnected from the network for a time.

In these or other embodiments, the system and method may include a rules-based engine or model that generates recommendations based on classification of the type of disconnection between the one or more medical systems and the at least one monitoring station. The recommendations may include, but are not limited to, information indicating a course of action to troubleshoot, remediate, or otherwise reestablish connection between the one or more medical systems and the at least one monitoring station, notify personnel of the disconnection and/or approaches to be taken regarding patient care during the period of failure, identifying false positives (e.g., battery swap), or use alternative or secondary/back-up systems as replacements during the period of disconnection or failure of the one or more medical systems.

FIG. 1 illustrates an example scenario for implementing the system and method embodiments. In this example, the system includes a monitoring station 110 and one or more medical systems 120 located in a medical facility such as a hospital, clinic, doctor office, out-patient facility, or another type of medical setting or installation. The monitoring station 110 may include a workstation with one or more computers, servers, wireless or handheld devices, or other type of processing system. Such equipment may be located, for example, at a nurses' station or a location of other hospital personnel, e.g., an administrator, information technology (IT) specialists, medical or diagnostic technicians, etc. In another embodiment, the monitoring station may be maintained by a medical service for patients and/or the elderly, a call center, doctor office, or another station related to monitoring the condition of a patient and/or medical systems, that may be located on-site or at a remote location from the medical system(s) being monitored.

The one or more medical systems 120 may include medical equipment or applications installed or otherwise controlling the medical equipment. In one embodiment, the applications may include clinical applications for a patient under observation. Examples include patient monitoring or diagnostic devices, medical information processing systems, surgical tools, x-ray machines, CAT scan or MRI systems, or other types of clinically or medically related equipment, including but not limited to intravenous drips, oxygen, and other patient drug delivery or life support systems. In one embodiment, the medical application is installed within a wearable device for purposes of monitoring vital signs and/or other characteristics of a patent.

The medical system(s) 120 may communicate with the monitoring station 110 over a network or other type of communications link 130. When the medical facility includes the medical systems and monitoring system, the network may be a wired or wireless local area network. In one implementation, the hospital may include multiple hot spots for supporting WiFi or other protocols for communicating information between the medical system(s) and the monitoring station. In another implementation, the monitoring station may be remotely located from the one or more medical systems. In this case, the medical system(s) may communicate with the monitoring station through a broadband network such as a virtual private network (VPN), cloud-based network, or other another type of network associated with the internet.

Figure 2:
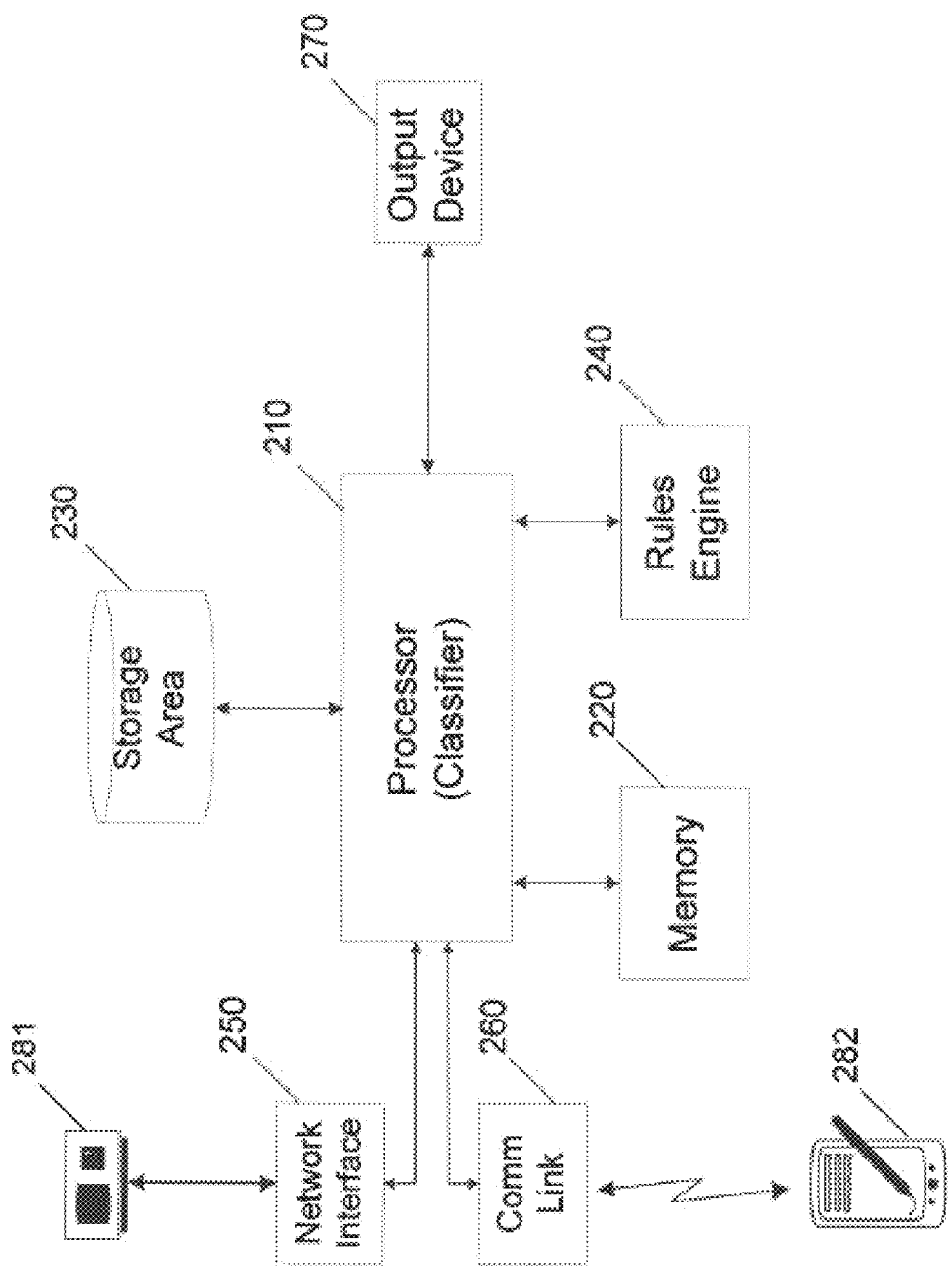
FIG. 2 illustrates an embodiment of a system for classifying disconnects.

FIG. 2 illustrates an embodiment of a system for classifying disconnects between one or more medical systems and at least one monitoring station, such as but not exclusively limited to the scenario illustrated in FIG. 1. The system may be included at the monitoring station or another location in communication with the monitoring station.

Referring to FIG. 2, the system includes a processor 210, a memory 220, a storage area 230, and a rules engine 240. The processor 210 executes instructions stored in the memory for implementing operations included in the embodiments described herein. The memory 230 may be a read-only memory, random access memory, or another type of non-transitory computer-readable medium storing the instructions. The memory may be resident with the processor or may be accessed remotely, for example, from a storage area network. In one embodiment, the processor may be a cloud-based processor for classifying one or more types of disconnects between the medical system(s) and monitoring station. In the example of FIG. 2, the system is at the monitoring station.

The memory 220 stores instructions which, when executed by the processor 210, implements a classifier for labeling the disconnects. The classifier may be, for example, a model-based classifier trained using machine-learning techniques based on an initial data set. The initial data set includes information indicative of the types of disconnects to be classified. Examples of models for the classifier include, but are not limited to, one implementing a logistic regression algorithm, a support vector machine (SVM), principal component analysis (PCA) algorithm, or another type of probabilistic or statistical model. In one embodiment, the processor may execute the instructions stored in the memory to implement a neural network, a predictive model, or another type of artificial intelligence based algorithm for classifying types of disconnects.

The storage area 230 may store one or more types of data. For example, the storage area may store one or more sets of training data for training the classifier implemented by the processor to classify types of disconnects relating to the medical system(s) and/or their applications. The training data includes information indicating different conditions, signals, signatures, waveforms, operating parameters, and/or other conditions or information that may be used as a basis for detecting and classifying predetermined types of disconnects. The training data may also include information that identifies false positives, in an effort to increase the accuracy of the classifier and thus the quality and effectiveness of patient care. Additionally, the storage area 230 may store contact information of various medical or technical personnel relating to the medical system(s), troubleshooting information for correcting or compensating for different disconnect scenarios, software patches for the medical applications that has been disconnected, and notification and/or alarm information as well as other information.

The rules engine 240 may store a collection of rules indicating what action(s) are to be taken when a disconnect has been detected and classified by the classifier 210. In one embodiment, the rules engine links predetermined recommendations to different types of classified disconnects. Because each disconnect, or disconnect type, may have its own distinctive features, the rules may link different recommendations for different disconnects/disconnect types. The recommendations generated by the rules engine 240 may also match the specific features of the medical system(s), or in the case where the disconnect relates to disconnect of a medical (e.g., clinical) application in a device, the specific features of the device. This is especially beneficial when the recommendations include remedial or troubleshooting actions that change from device manufacture to device manufacture.

The system may be implemented to monitor the medical system(s) through one or more corresponding wired or wireless connections. For example, the system may include one or both of a network interface 250 and a communications link 260. The network interface may be a WiFi interface for wirelessly transmitting signals to and/or receiving signals from at least one medical system 281. In this case, the medical system is a monitor for taking the vital signs of a patient in a hospital room. In this case, the network may be, for example, a local area network of the hospital or a secure VPN. The communications link 260 may transmit signals to and/or receive signals from a handheld, battery-operated medical monitor 282 for a patient. The communications link may conform to a short-range protocol for purposes of sending and receiving information to and from the processor 210.

The medical system 281 and/or 282 may operate based on a stored medical application or other type of software which must not be offline or otherwise disconnected from the processor during monitoring. This may happen in a variety of circumstances. For example, the medical application may be disconnected from the processor when the host device (e.g., medical system 282) is malfunctioning or when the host device has lost its wireless connection to the network or communications link. In another case, the application itself may be corrupted or otherwise malfunction, either permanently or periodically. These types of disconnections may occur, for example, during a software update, a calibration process, a reboot, low battery power, or when the application is otherwise considered to be offline. In some cases, the application may not be disrupted or cease from operating even through the host device (medical system) goes offline (e.g., loses the network connection) for a short period of time. In this case, when the host device reconnects to the network, the application continues running as if the host device never experienced an interruption. In this case, the classifier may be trained to not acknowledge a disconnect under these circumstances. Additional examples of when the application and/or host device may be disconnected and how the different types of disconnection are classified by the processor 210 are discussed in greater detail below.

In addition to the foregoing features, the system may also include an output device 270 for outputting results of the detection, the type of classified disconnect, and/or a recommendation for remediating the disconnect based on a decision rendered by the rules engine. In one embodiment, the output device may include a display at the monitoring station for displaying the aforementioned information in textual, graphical, or other representative form. In one embodiment, the processor may access and display troubleshoot, contact, or other information for reestablishing connection to the medical application and/or host device with the classification and/or recommendation information. In one embodiment, this information may be sent to the device of a remotely located technician (either wirelessly or through a wired connection) where the host device (medical system) is located so that connection can be reestablished. In another embodiment, the information may be sent to a technician center for dispatching personnel to fix the problem or otherwise reestablished connection to the monitoring station processor.

Figure 3:
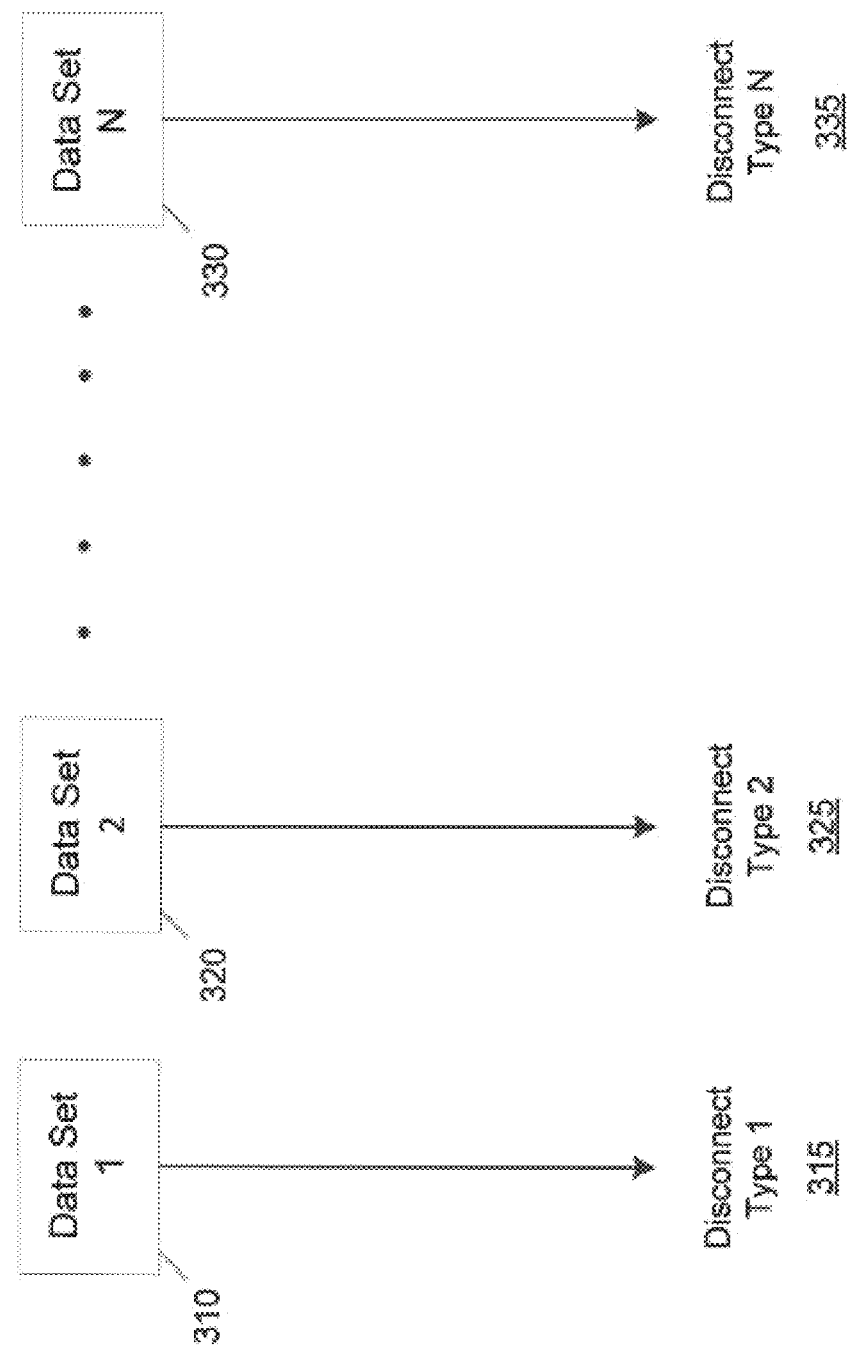
FIG. 3 illustrates an example of training data for a classifier.

FIG. 3 illustrates an example of how the classifier implemented by processor 210 may be trained to detect and classify disconnects between one or more medical systems and the monitoring station. Referring to FIG. 3, after a specific type of model or algorithm for the classifier has been selected, the classifier may be trained with one or more data sets. The data sets may include one or more parameters and/or other type of information that may be used as a basis for determining whether data input to the classifier likely corresponds to a particular type of disconnect. For example, when a first one or combination of input parameters and/or information 310 exist, the classifier is trained to generate a result indicating that a first type of disconnect 315 likely exists. When a second one or combination of input parameters and/or information 320 exist, the classifier is trained to generate a result indicating that a second type of disconnect 325 likely exists. The classifier may be trained with additional data sets (e.g., up to N data sets) 330 to indicate an additional corresponding number of disconnect types 335. Some or all of the data sets may be used to train the classifier to detect application disconnects. In this or another embodiment, one or more of the data sets may train the classifier to detect other types of disconnects, including but not limited to device disconnects.

Figure 4:
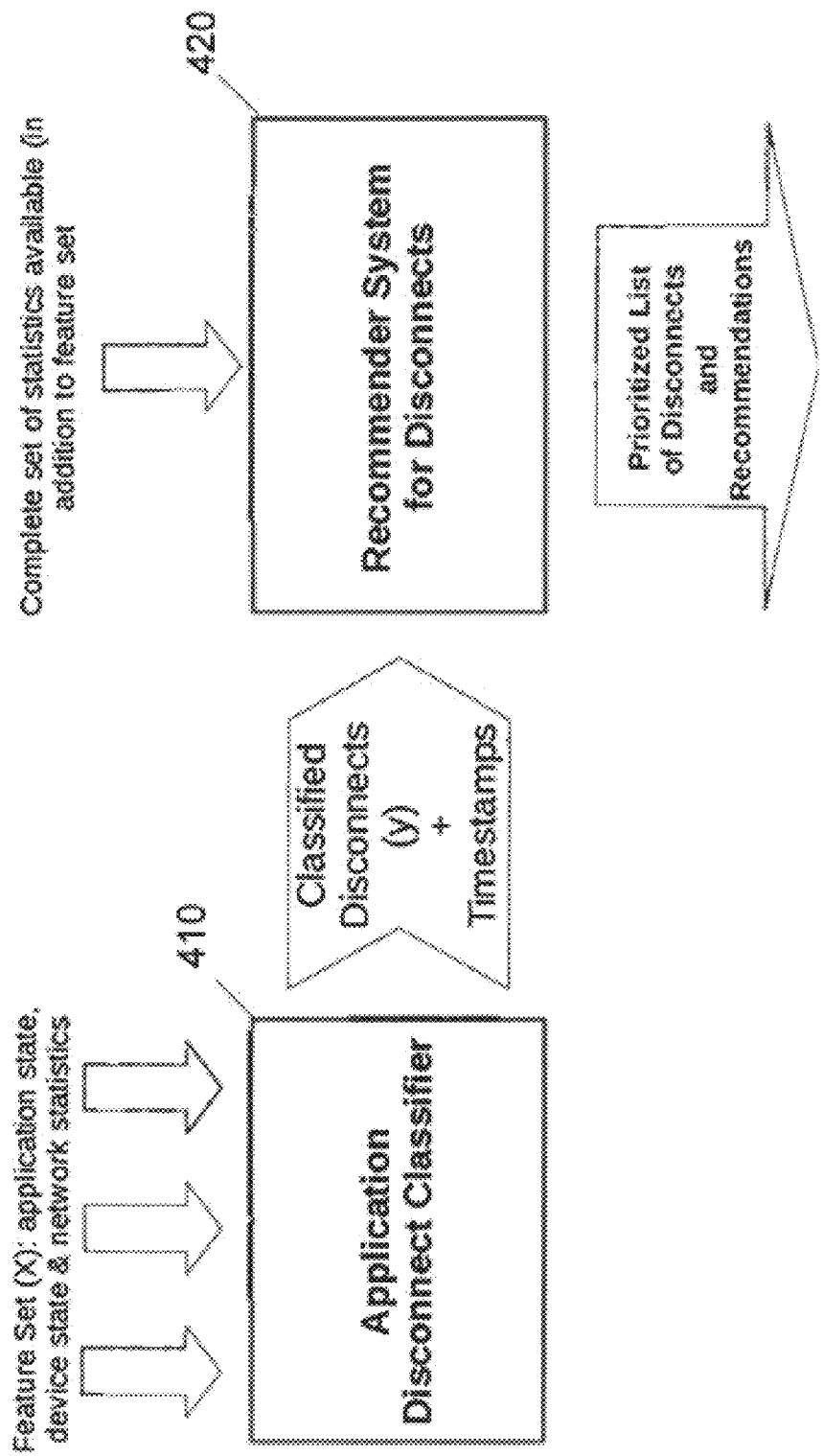
FIG. 4 illustrates an embodiment of a classifier and recommender.
Figure 5:
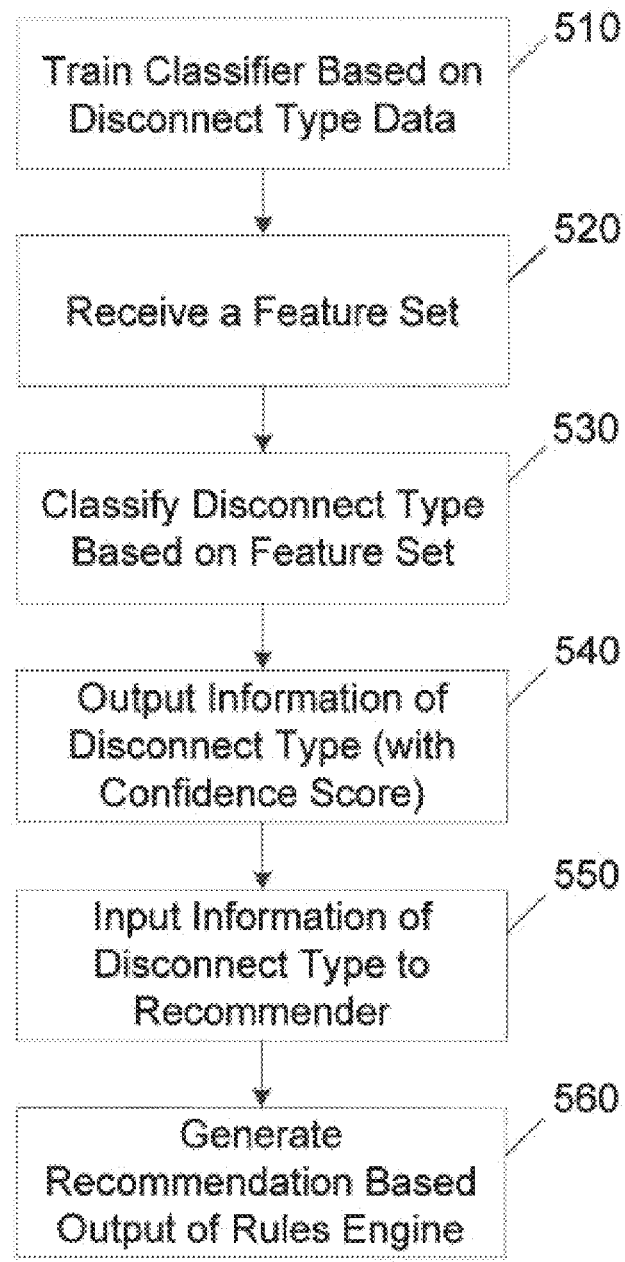
FIG. 5 illustrates an embodiment of a method for classifying disconnects.

FIG. 4 illustrates an embodiment of a system for classifying disconnects between one or more medical systems and at least one monitoring station. FIG. 5 illustrates an embodiment of a method for classifying disconnects that may be performed, for example, by the system of FIG. 4. These system and method embodiments perform classification of application-type disconnects using a classifier trained by machine-learning techniques applied to one or more data sets, which in these embodiments may include data sets called feature sets. The processor of this embodiment may also generate recommendations or indicate other courses of action based on the classified type of disconnect using, for example, a rules engine as previously described.

Referring to FIGS. 4 and 5, the system includes a classifier 410 and a recommender 420. The classifier 410 may be any of the types of classifiers described herein. At 510, the classifier 410 is initially trained based on data corresponding to respective ones of a plurality of disconnect types to be classified. Once the classifier is trained, it is put into practice for purposes of monitoring disconnects between at least one monitoring station and one or more medical systems. In this embodiment, the one or more medical systems may include one or more patient-wearable devices controlled by an operating system or application that performs a specific medically related function.

At 520, the classifier 41 receives a feature set that includes various types of information arranged in a predetermined format, e.g., in a packet that includes one or more predetermined fields dedicated to store corresponding types of information. In one example implementation, the packet may include one or more bits (e.g., in a predetermined header field) indicating that a disconnection has occurred. For example, the monitoring station software may receive information from a clinical application server that the device is in a connected or disconnected state.

The feature set may include all or a portion of the following categories of information relating to a device equipped with an application connected to (or otherwise operating or interfacing in conjunction with) the monitoring station through a network: (1) clinical/medical application state, (2) device state, and (3) network state.

The clinical/medical application state features may include, for example, technical features relating to the application in the device. Examples of the technical features of a patient worn monitor (PWM) device include disconnect time from a central server (e.g., monitoring station), percent wave data loss (e.g., application data loss), the amount of wave data recovery activity (e.g., application data recovery), and operating mode of the application and/or device. In one embodiment, features such as disconnect time, percent wave data loss, etc., may be divided into different levels or categories. Also, the PWM device may send real-time data to a clinical application server for review at, for example, a nurses station.

The different levels or categories of the technical features may, alone or taken in combination with other features, be indicative of different states of the clinical/medical application. The classifier may be trained to detect and classify types of disconnects based on these different levels, or combinations of different levels or categories of the technical features. Examples of these different levels or categories may be as follows.

| Disconnect Time | % Wave Data Loss | Data Recovery | Mode |
| --- | --- | --- | --- |
| First Time Range | First Loss Range | First Range | First Mode |
| Second Time Range | Second Loss Range | Second Range | Second Mode |
| Third Time Range | Third Loss Range | Third Range | Third Mode |

In addition to these features, there may also be a timeliness factor in one or more embodiments. The timeliness factor may indicate, for example, a percentage of wave data loss that occurred in a last time period before and/or after the application disconnect occurred. Examples of the last time period include the last 30 seconds, 1 minute, 5 minutes, and/or another time period.

The operating modes may be different for different devices. For example, the operating modes of a wearable device may be different from one or more operating modes of another type of device for which disconnects are to be classified. Examples of the modes of a wearable device include monitoring mode, telemetry mode, transport mode, standby mode, service mode, or application software upgrade mode. Other devices to be monitored may have one or more different modes.

The device state features may be separate from the state of the application and may relate, for example, to operational characteristics of the device. Examples of the device state features for a PWM device include percent battery level, battery life or number of charge cycles, percent central processing unit (CPU) utilization, and uptime since last reboot. Different levels or categories of the operational characteristics may, alone or taken in combination with other features, be indicative of different states of the device state. The classifier may be trained to detect and classify types of disconnects based on these different levels, or combinations of different levels or categories of the operational characteristics of the device. Examples of these different levels or categories may be as follows.

| % Battery Level | Battery Life/Cycles | % CPU Usage | Reboot Uptime |
| --- | --- | --- | --- |
| First % Range | First L/C Range | First % Range | First Time Range |
| Second % Range | Second L/C Range | Second % Range | Second Time Range |
| Third % Range | Third L/C Range | Third % Range | Third Time Range |

The network statistics features may be categorized into wired and wireless statistics. Examples for a PWM implementation include (1) Percent IEEE 802.11 RX CRC errors, (2) Percent IEEE 802.11 Retries, (3) Percent Failed IEEE 802.11 TX count, (4) Radio signal level, (5) IEEE 802.11 missed beacon count, (6) number of network disconnects, (7) percent TCP/IP retries, (8) percent TCP/IP RX CRC errors, and (9) number of recent roams. This and other information may be communicated, for example, to a nurses station over a wireless local area network (WLAN) or another types of communications network. Different levels or categories of the network statistic features may, alone or taken in combination with other features, be indicative of different states of the network. The classifier may be trained to detect and classify types of disconnects based on these different levels, or combinations of different levels or categories of network statistics. Examples of these different levels or categories may be as follows, where L1 corresponds to a first range level or category, L2 corresponds to a second range level or category, and L3 corresponds to a third range level or category.

| (1) | (2) | (3) | (4) | (5) | (6) | (7) | (8) | (9) |
|-----|-----|-----|-----|-----|-----|-----|-----|-----|
| L1  | L1  | L1  | L1  | L1  | L1  | L1  | L1  | L1  |
| L2  | L2  | L2  | L2  | L2  | L2  | L2  | L2  | L2  |
| L3  | L3  | L3  | L3  | L3  | L3  | L3  | L3  | L3  |

At 530, the classifier classifies the type of disconnect based on the features and/or other information in the received feature set. In one embodiment, the feature set input into the classifier may have only one feature or may have a combination of features. For example, the input feature set may have the following combination of features which the classifier is trained to identify as a first disconnect type.

Figure 6:
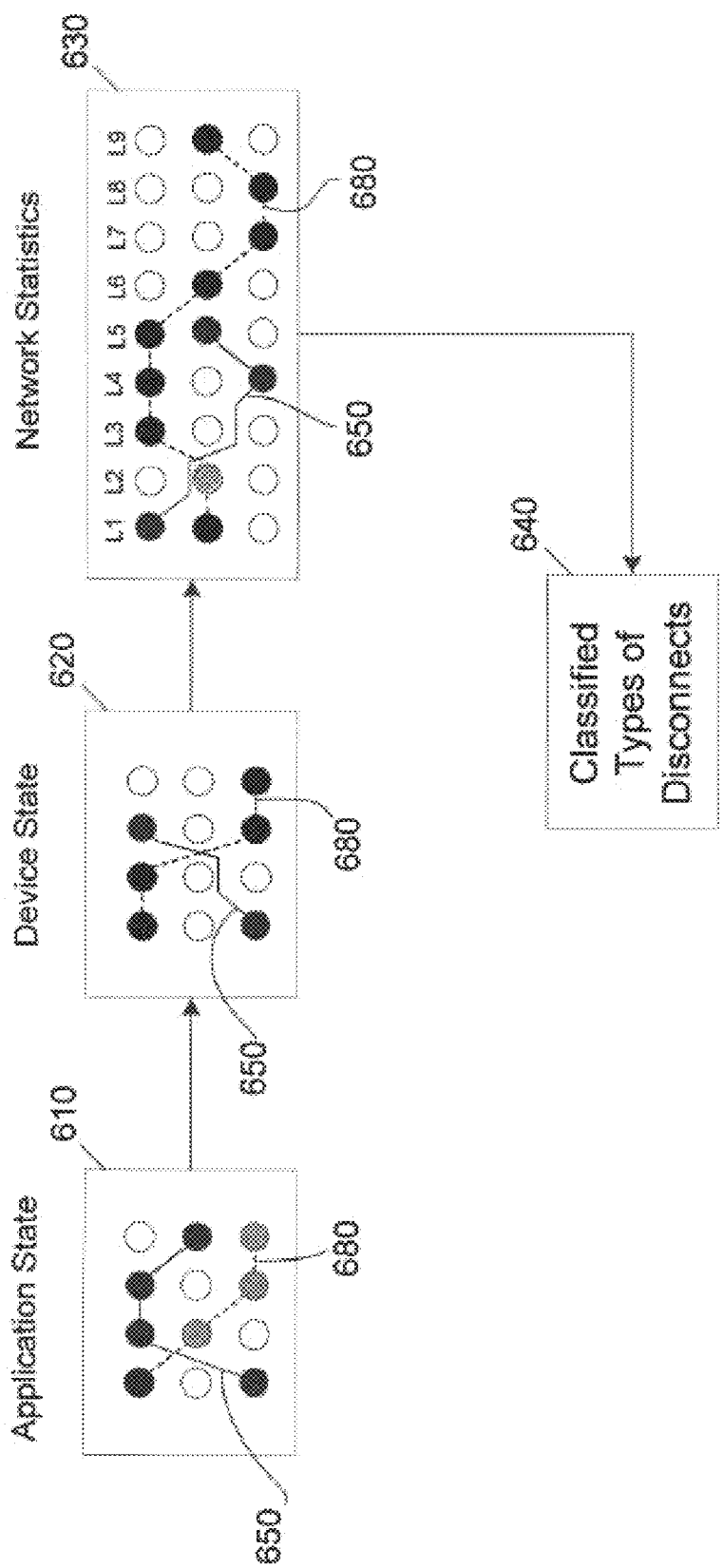
FIG. 6 illustrates an example of logic for classifying a disconnect.

FIG. 6 illustrates an example of the logical flow of the classifier 410 used to classify the type of disconnect of the input feature set. In FIG. 6, the classifier includes a first logical section 610 corresponding to the application state features, a second logical section 620 corresponding to the device state features, and a third logical section 630 corresponding to the network statistics section 630. Each of the first, second, and third logical sections include indicia (in this case, circles) that correspond to respective ones of the features identified above. Once the classification is computed, the classifier 410 may output information 640 indicating the classification result. The classifier may be trained to identify other types of disconnects based on different input feature sets.

Application State Features
  Disconnect Time: Third Time Range
  % Wave Data Loss: First Loss Range
  Date Recovery: First Range
  Mode: Second Mode
Device State Features
  % Battery Level: Third % Range
  % CPU Usage: First % Range
Network Statistics Features
  (1): L1
  (4): L3
  (5): L2

This example illustrates that the input features do not have to include all the features in all the categories of features. For example, the input feature set omits battery life/cycles and reboot uptime for the device state category and omits information corresponding to features (2), (3), (6), (7), (8), and (9) of the network statistics category. The features in the input feature set that are included and relied on by the classifier 410 to compute the classification correspond to the darkened circles in the sections with a connecting logical flow line 650 (solid line) in FIG. 6. By way of example, a logical flow line linking features included in another input feature set corresponding to connecting logical flow line 680 (dotted line), which produces a different type of disconnect classification performed by the classifier.

Even with these omissions, the classifier 410 has been trained to classify (e.g., with a computed likelihood) that the input feature set is indicative of a certain one of the disconnect types. In other embodiments, the classifier 410 classifies input feature sets that include data corresponding to all of the features of all the categories or data corresponding to a different combination of features that represents less than all the features in all categories.

In one embodiment, the disconnect type may partially or wholly depend on the device type. In this case, the classified disconnect may be specific to that device only. For example, when the medical system (device) is a bedside patient monitor, one type of classified disconnection that would not exist for this device is a battery swap because a bedside monitor does not have a battery.

Returning to FIGS. 4 and 5, at 540, the classifier 410 outputs information indicating the type of disconnect that the classifier determined the input feature set corresponds to. The following is an example list of the types of disconnects that may be classified by the classifier. In other embodiments, the classifier may be generated using machine-learning techniques to classify different list of disconnect types.

Disconnect Type 1: Battery Replacement
  Disconnect Type 2: Radio Software Reset
  Disconnect Type 3: Device Reboot/Watchdog Reset
  Disconnect Type 4: Power Cycle
  Disconnect Type 5: Device in Standby Mode
  Disconnect Type 6: Application Restart
  Disconnect Type 7: Network Congestion or Other Issue
  Disconnect Type 8: Device/Patient Out-of-Coverage Area
  Disconnect Type 9: Device Shut Down or Out-of-Service
  Disconnect Type 10: Device Software Crash
  Disconnect Type 11: Intermittent Wireless Issue
  Disconnect Type 12: Intermittent Wired Issue In one embodiment, the classifier may compute a confidence score for the disconnect type that was classified based on the input feature set. The confidence score may be 100%, for example, when there is an exact match between the information in the input feature set and the feature set stored of the disconnect type identified by the classifier. When there is not an exact match between the input feature set and the feature sets stored for the disconnect types, the classifier may generate a list of possible disconnect types with corresponding confidence scores. When the classifier implements a supervised machine-learning algorithm, the confidence scores may be generated, for example, based on coefficients assigned to each feature in the feature set. In one embodiment, the confidence scores may be computed by a machine-learning algorithm, example tutorials of which are known and available on the internet. The list of possible disconnects may be prioritized in a predetermined order, starting with the highest confidence score. The list may be output on a display screen, for example, at the monitoring station and/or output to one or more predetermined personnel.

At 550, once the classifier has classified the feature set as corresponding to a particular one of a plurality of predetermined disconnect types (y), the classifier may input this information into the recommender 420. In one embodiment, the recommender may include a rules-based engine as previously described. The rules-based engine may also receive timestamp information of the disconnect from the classifier 410 along with the information indicating the classified disconnect type.

At 560, the recommender 420 may process the disconnect type classified by the classifier to generate a recommendation on a course of action to be taken for the classified type of disconnect. In one embodiment, the recommender 420 may include a rules engine which matches the type of classified disconnect to one or more predetermined rules. The rules may indicate how the classified disconnect may be managed. Examples of how the disconnect may be managed include providing instructions for use by technical personnel on how to reestablish connection of the medical system to the monitoring station, instructions to be transmitted to a network manager and/or the medical system for automatically correcting the disconnect, issuance of notifications or alarms to (remotely located or on-site) personnel for correcting the disconnection, an notice indicating that the device is malfunctioning or broken and thus needs to be replaced, an indication that the application in the device needs updating or is malfunctioning in one or more ways, and/or another recommendation for remedying the problem associated with the disconnect.

When operating with a rules-based engine, the recommender 420 (e.g., a processor executing an application at the server or workstation of the monitoring station) accesses and matches the classified disconnect against a predetermined set of rules included in information stored in a database. In one embodiment, the recommender may initially sort the results of the classifier based on severity and/or likelihood that the disconnect is actionable or not. For non-actionable disconnects, the recommender 420 may provide an explanation to a technician that can be used for possibly optimizing a clinical workflow. For actionable disconnects, the recommender system may recommend a number of predetermined actions (e.g., as determined by rules of the rules engine).

In one embodiment, the recommendations may (a) provide directive to contact manufacturer support or business unit that is the developer of the device, (b) include one or more actions for improving the network infrastructure, and (c) for disconnects for which the root cause is not immediately clear, perform an additional analysis (e.g., using a PCA model) to find correlations on where to investigate further. The following table provides a more detailed listing of examples of recommendations that may be generated by the recommender 420 for various disconnect types.

| Disconnect Type | Severity | Recommendation/Explanation | Additional Analytics that Could Be Provided |
| --- | --- | --- | --- |
| Battery Swap | Low | Battery was intentionally swapped by a clinician. | |
| Device Out-of-Service | Low | Device has been intentionally taken out-of-service and possibly stored away. | Length out-of-service |
| Exit from Standby Mode | Low | The device will intentionally restart the application when standby is exited. | |
| Out-of-Coverage Area | Medium | The device left the coverage area. This may be expected or may indicate a gap in the coverage area. | Last access point (AP) connection and signal level before leaving the coverage area First AP connection and signal level after returning to the coverage area |
| Power Cycle | Medium | The device was reset and this does not appear to be related to a watchdog reset or battery swap. This could be the result of the device being dropped, accidental battery removal or a clinician purposely reinserting the battery. | |
| Radio Software Reset | High | The device's radio was unexpectedly reset. Recommend to contact Philips support. | Anomalous network statistics observed before the reset |
| Device Watchdog Reset | High | The device was unexpectedly reset by the watchdog. Recommend to contact Philips support. | Anomalous statistics observed before the rest |
| Application Restart | High | The application unexpectedly crashed and recovered. Recommend to contact Philips support. | Anomalous statistics observed before the rest |
| Network Issue | Medium -High | A network issue caused the application to disconnect. | Based on the statistics, this disconnect could be further divided into wired or wireless network issues. |

-continued

| Disconnect Type | Severity | Recommendation/Explanation | Additional Analytics that Could Be Provided |
| --- | --- | --- | --- |
| | | | Analysis such as PCA or anomaly detection could be performed over the entire available statistics set for this disconnect type to see if there is a correlation that can point to the nature of the event. |

When there is not an exact match between the disconnect types of the classifier and the input feature set, the classifier 410 may automatically input the most likely disconnect type (e.g., the disconnect type with the highest confidence score) to the recommender 420. In one embodiment, the classifier may output a prioritized list of disconnect types on a screen at the monitoring system and a technician may select the disconnect type to be input into the recommender. The prioritized list of disconnects and their corresponding recommendations may be output for display and then an electronic record may be stored to memorialize the event and for tracking purposes. In one embodiment, the disconnect types and corresponding recommendations may be output on a dashboard of an application on a workstation computer and reports may be generated on a periodic basis to allow for review of all disconnect types detected and classified.

In accordance with one or more of the aforementioned embodiments, a machine-learning based solution is provided that classifies application-level disconnects for medical devices. These classified disconnects may then be used by the hospital staff, field server engineers, or other personnel to quickly hone in on disconnect behavior that requires action. The solution is in the form of a method and system which apply model-based, machine-learning techniques to determine the disconnect type based on an input feature set. Through these techniques, the system and method are able to determine the disconnect type in a way that cannot be determined through mental processes. Also, the system and method may implement a recommender that generates (e.g., using a rules-based engine) one or more recommendations for resolving the disconnect type once it has been classified.

The system and method embodiments may be extendable such that, the development team of the manufacturer may provide the features (e.g., feature sets, data sets, input parameters, etc.) and disconnect types (labels) applicable to the device for each new medical system or device to be monitored. The classifier may then be trained based on these features, thereby avoiding the need to develop specialized code/modules for each product and using instead the machine-learning model to classify the application disconnect types.

The methods, processes, and operations of the system embodiments described herein may be performed by code or instructions to be executed by a computer, processor, controller, or other signal processing device. The code or instructions may be stored in the non-transitory computer-readable medium as previously described in accordance with one or more embodiments. Because the algorithms that form the basis of the methods (or operations of the computer, processor, controller, or other signal processing device) are described in detail, the code or instructions for implementing the operations of the method embodiments may transform the computer, processor, controller, or other signal processing device into a special-purpose processor for performing the methods herein.

The processors, models, algorithms, classifiers, recommenders, rules engines, and/or other signal, pattern, or data detection, signal generating, or signal processing features of the embodiments disclosed herein may be implemented in logic which, for example, may include hardware, software, or both. When implemented at least partially in hardware, expert systems, processors, detectors, models, or other signal, pattern, or data detection, signal generating, or signal processing features may be, for example, any one of a variety of integrated circuits including but not limited to an application-specific integrated circuit, a field-programmable gate array, a combination of logic gates, a system-on-chip, a microprocessor, or another type of processing or control circuit.

When implemented in at least partially in software, the processors, models, algorithms, classifiers, recommenders, rules engines, and/or other signal, pattern, or data detection, signal generating, or signal processing features may include, for example, a memory or other storage device for storing code or instructions to be executed, for example, by a computer, processor, microprocessor, controller, or other signal processing device. The processors, models, algorithms, classifiers, recommenders, rules engines, and/or other signal, pattern, or data detection, signal generating, or signal processing features may be those described herein or one in addition to the elements described herein. Because the algorithms that form the basis of the methods (or operations of the computer, processor, microprocessor, controller, or other signal processing device) are described in detail, the code or instructions for implementing the operations of the method embodiments may transform the computer, processor, controller, or other signal processing device into a special-purpose processor for performing the methods herein.

Although the various exemplary embodiments have been described in detail with particular reference to certain exemplary aspects thereof, it should be understood that the invention is capable of other example embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

We claim:

1. A method for processing information, comprising:
receiving a feature set for an application in a medical system;
determining a disconnection between the application and a monitoring station; and
determining a type of the disconnection based on information in the feature set, wherein the information in the feature set includes a plurality of categories of information relating to the application, each category in the plurality of categories of information being indicative of a different parameter relating to the disconnection,
wherein the plurality of categories of information include at least two of a first category including a plurality of application state features, a second category including a plurality of device state features, or a third category including a plurality of network statistics features, and
wherein determining the type of disconnection includes inputting the feature set into a classifier trained to automatically determine the type of disconnection based on a predetermined combination of one or more of the application state features of the first category, one or more of the device state features of the second category, and/or one or more of the network statistics features of the third category in the feature set.

2. The method of claim 1, further comprising:
generating a confidence score indicating a probability for the type of the disconnection automatically determined by the classifier.

3. The method of claim 1, further comprising:
generating information indicative of a recommended course of action for the type of the disconnection determined by the classifier.

4. The method of claim 3, wherein generating the information includes:
inputting information indicative of the type of the disconnection into a rules-based engine,
wherein the rules-based engine matches the type of the disconnection to at least one predetermined rule that corresponds to the recommended course of action.

5. The method of claim 1, further comprising:
outputting information of the type of the disconnection on a display at the monitoring station.

6. The method of claim 5, wherein the monitoring station is at one of a technical support location, a nurses station, or a medical monitoring facility.

7. A system for processing information, comprising:
a memory configured to store instructions; and
a processor configured to execute the instructions to:
receive a feature set for an application in a medical system;
determine a disconnection between the application and a monitoring station; and
determine a type of the disconnection based on information in the feature set,
wherein the information in the feature set includes a plurality of categories of information relating to the application, wherein each category in the plurality of categories of information is indicative of a different parameter relating to the disconnection,
wherein the plurality of categories of information include at least two of a first category including a plurality of application state features, a second category including a plurality of device state features, or a third category including a plurality of network statistics features, and
wherein the processor is configured to determine the type of the disconnection based on a classifier trained to automatically determine the type of the disconnection based on a predetermined combination of one or more of the application state features of or more of the network statistics features of the third category in the feature set.

8. The system of claim 7, wherein the processor is configured to execute the instructions to generate a confidence score indicating a probability for the type disconnection the automatically determined by the classifier.

9. The system of claim 7, wherein the processor is configured to execute the instructions to generate information indicative of a recommended course of action for the type of the disconnection determined by the classifier.

10. The system of claim 9, wherein generating the information includes:
inputting information indicative of the type of disconnection into a rules-based engine,
wherein the rules-based engine matches the type of disconnection to at least one predetermined rule that corresponds to the recommended course of action.

11. The system of claim 7, wherein the processor is configured to execute the instructions to output information indicative of the type of the disconnection on a display at the monitoring station.

12. The system of claim 11, wherein the monitoring station is at one of a technical support location, a nurses station, or a medical monitoring facility.

13. A non-transitory computer readable medium storing instructions that, when executed by a processor, cause the processor to:
receive a feature set for an application in a medical system;
determine a disconnection between the application and a monitoring station; and
determine a type of the disconnection based on information in the feature set,
wherein the information in the feature set includes a plurality of categories of information relating to the application, each category in the plurality of categories of information being indicative of a different parameter relating to the disconnection,
wherein the plurality of categories of information include at least two of a first category including a plurality of application state features, a second category including a plurality of device state features, or a third category including a plurality of network statistics features, and
wherein the type of the disconnection is determined by inputting the feature set into a classifier trained to automatically determine the type of the disconnection based on a predetermined combination of one or more of the application state features of the first category, one or more of the device state features of the second category, and/or one or more of the network statistics features of the third category in the feature set.

14. The non-transitory computer readable medium of claim 13, wherein the instructions further cause the processor to generate a confidence score indicating a probability for the type of the disconnection automatically determined by the classifier.

15. The non-transitory computer readable medium of claim 13, wherein the instructions further cause the processor to generate information indicative of a recommended course of action for the type of the disconnection determined by the classifier.

16. The non-transitory computer readable medium of claim 15, wherein the instructions cause the processor to generate the information by inputting information indicative of the type of the disconnection into a rules-based engine, wherein the rules-based engine matches the type of the disconnection to at least one predetermined rule that corresponds to the recommended course of action.

17. The non-transitory computer readable medium of claim 13, wherein the instructions further cause the processor to output information indicative of the type of the disconnection on a display at the monitoring station.

18. The non-transitory computer readable medium of claim 17, wherein the monitoring station is at one of a technical support location, a nurses station, or a medical monitoring facility.

\* \* \* \* \*